US007827990B1

(12) United States Patent
Melidis et al.

(10) Patent No.: US 7,827,990 B1
(45) Date of Patent: Nov. 9, 2010

(54) SEALING LIP DEVICE FOR A RESPIRATORY MASK, RESPIRATORY MASK AND A METHOD AND A MOULD FOR PRODUCING THE SAME

(75) Inventors: Paris Melidis, Olching (DE); Theodor Lauboeck, Hohenbrunn (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 0 days.

(21) Appl. No.: 10/220,018

(22) PCT Filed: Feb. 25, 2000

(86) PCT No.: PCT/EP00/01586

§ 371 (c)(1),
(2), (4) Date: Jan. 30, 2003

(87) PCT Pub. No.: WO01/62326

PCT Pub. Date: Aug. 30, 2001

(51) Int. Cl.
*A62B 18/08* (2006.01)

(52) U.S. Cl. .................................................. 128/206.24

(58) Field of Classification Search ............ 128/204.24, 128/207.11, 201.22–201.24, 205.25, 206.12, 128/206.16, 206.23

See application file for complete search history.

(56) References Cited

U.S. PATENT DOCUMENTS

| 2,130,555 | A | 9/1938 | Malcom |
|---|---|---|---|
| 2,133,699 | A | 10/1938 | Heidbrink |
| 2,428,451 | A | 10/1947 | Emerson |
| 2,625,155 | A * | 1/1953 | Engelder ................ 128/206.24 |
| 2,706,983 | A | 4/1955 | Matheson et al. |
| 2,931,356 | A | 4/1960 | Schwarz |

(Continued)

FOREIGN PATENT DOCUMENTS

DE 4233448 4/1993

(Continued)

OTHER PUBLICATIONS

European Search Report, EP Application No. 09003544.5, dated Jun. 2, 2009.

*Primary Examiner*—Anhtuan T Nguyen
*Assistant Examiner*—Tuan V Nguyen
(74) *Attorney, Agent, or Firm*—Nixon & Vanderhye P.C.

(57) ABSTRACT

The invention relates to a sealing lip device for a respiratory mask, to a respiratory mask per se and to a method and mould for producing the same. According to the invention, the respiratory mask has an orifice (2) for receiving at least the nose tip of the mask wearer and a sealing lip (3) consisting of an elastomeric material, which surrounds the orifice and crosses the bridge of the nose. Said sealing lip has a supporting zone which lies against the face of a mask wearer. The elastic pliability of the sealing lip (3) is such that the sealing lip zone (a) which seals the area around the bridge of the nose has a greater pliability than the sealing lip zone (b1, b2, c) which lies adjacent to the nostrils and/or the upper lip of the mask wearer, when the mask is applied to the face of the latter. From a production method viewpoint, the synthetic material is introduced in two separate injection-moulding steps, a support structure (4) with thick walls being preferably configured in the first step.

35 Claims, 13 Drawing Sheets

U.S. PATENT DOCUMENTS

Figure 1:
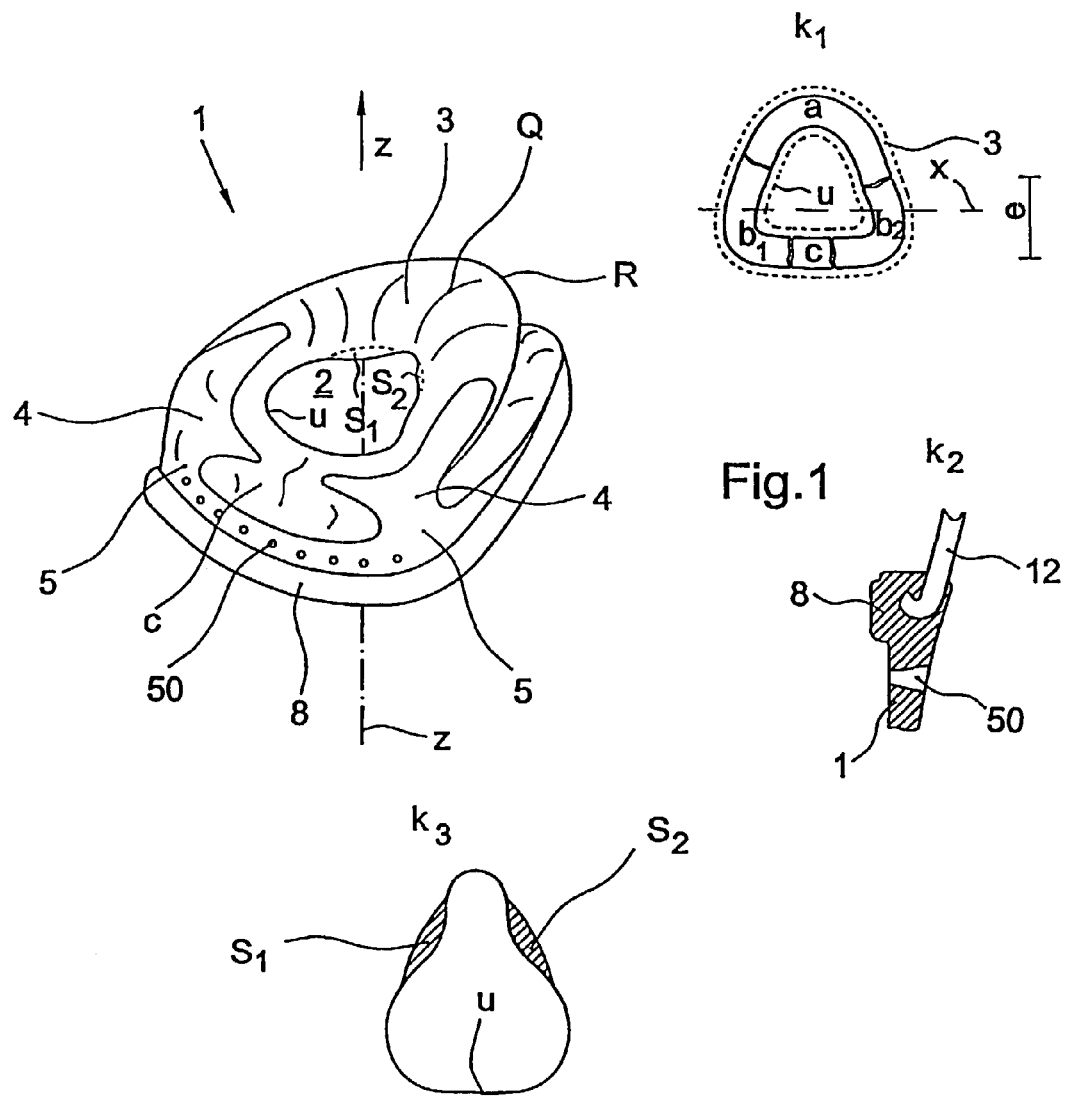

| | | | | |
|---|---|---|---|---|
| 4,062,357 | A | * 12/1977 | Laerdal | 128/206.26 |
| 4,069,516 | A | 1/1978 | Watkins, Jr. | |
| 4,265,239 | A | 5/1981 | Fischer, Jr. et al. | |
| 4,328,797 | A | * 5/1982 | Rollins et al. | 128/206.21 |
| 4,770,169 | A | 9/1988 | Schmoegner et al. | |
| 4,907,584 | A | * 3/1990 | McGinnis | 128/206.24 |
| 4,971,051 | A | 11/1990 | Toffolon | |
| 5,062,421 | A | * 11/1991 | Burns et al. | 128/205.27 |
| 5,074,297 | A | 12/1991 | Venegas | |
| 5,243,971 | A | 9/1993 | Sullivan et al. | |
| 5,349,949 | A | * 9/1994 | Schegerin | 128/206.24 |
| 5,391,248 | A | * 2/1995 | Brain | 156/242 |
| 5,540,223 | A | * 7/1996 | Starr et al. | 128/205.25 |
| 5,649,532 | A | 7/1997 | Griffiths | |
| 5,662,101 | A | 9/1997 | Ogden et al. | |
| 5,921,239 | A | * 7/1999 | McCall et al. | 128/205.25 |
| 5,935,136 | A | * 8/1999 | Hulse et al. | 606/123 |
| 5,975,079 | A | * 11/1999 | Hellings et al. | 128/206.24 |
| 6,016,804 | A | 1/2000 | Gleason et al. | |
| 6,112,746 | A | * 9/2000 | Kwok et al. | 128/207.13 |
| 6,412,487 | B1 | 7/2002 | Gunaratnam et al. | |
| 6,467,483 | B1 | * 10/2002 | Kopacko et al. | 128/207.12 |
| 6,513,526 | B2 | * 2/2003 | Kwok et al. | 128/206.24 |
| 6,626,177 | B1 | * 9/2003 | Ziaee | 128/206.21 |

FOREIGN PATENT DOCUMENTS

| | | | |
|---|---|---|---|
| DE | 196003949 | 8/1997 | |
| EP | 0 334 555 | 9/1989 | |
| EP | 0 303 090 B1 | 4/1992 | |
| EP | 0747078 | 12/1996 | |
| EP | 0 853 962 A2 | 7/1998 | |
| GB | 649689 | 1/1951 | |
| JP | 11-397 A | 1/1999 | |
| JP | 11000397 A | 1/1999 | |
| WO | 98/04310 | * 2/1998 | 128/206.24 |
| WO | WO98/04310 | 2/1998 | |
| WO | WO 98/34665 | 8/1998 | |

\* cited by examiner

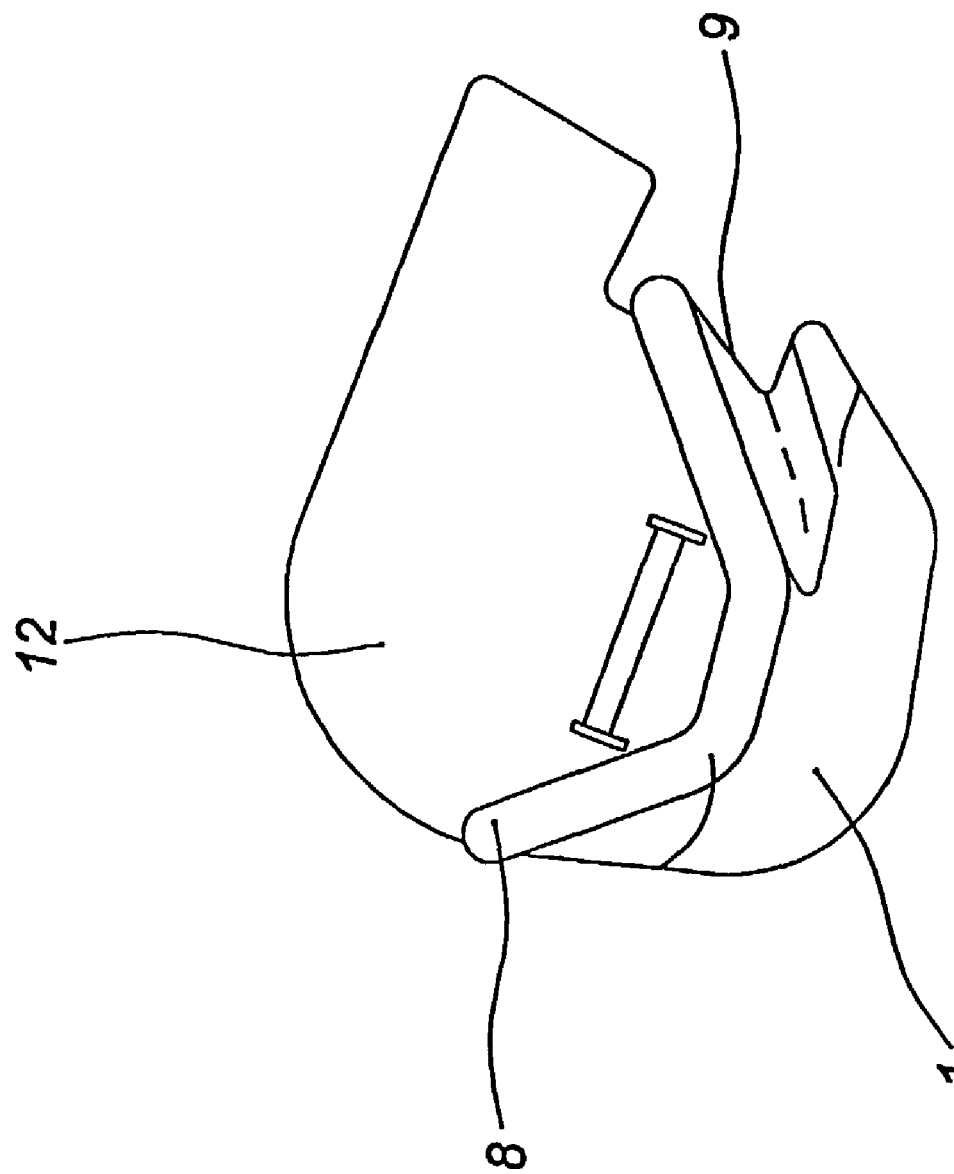

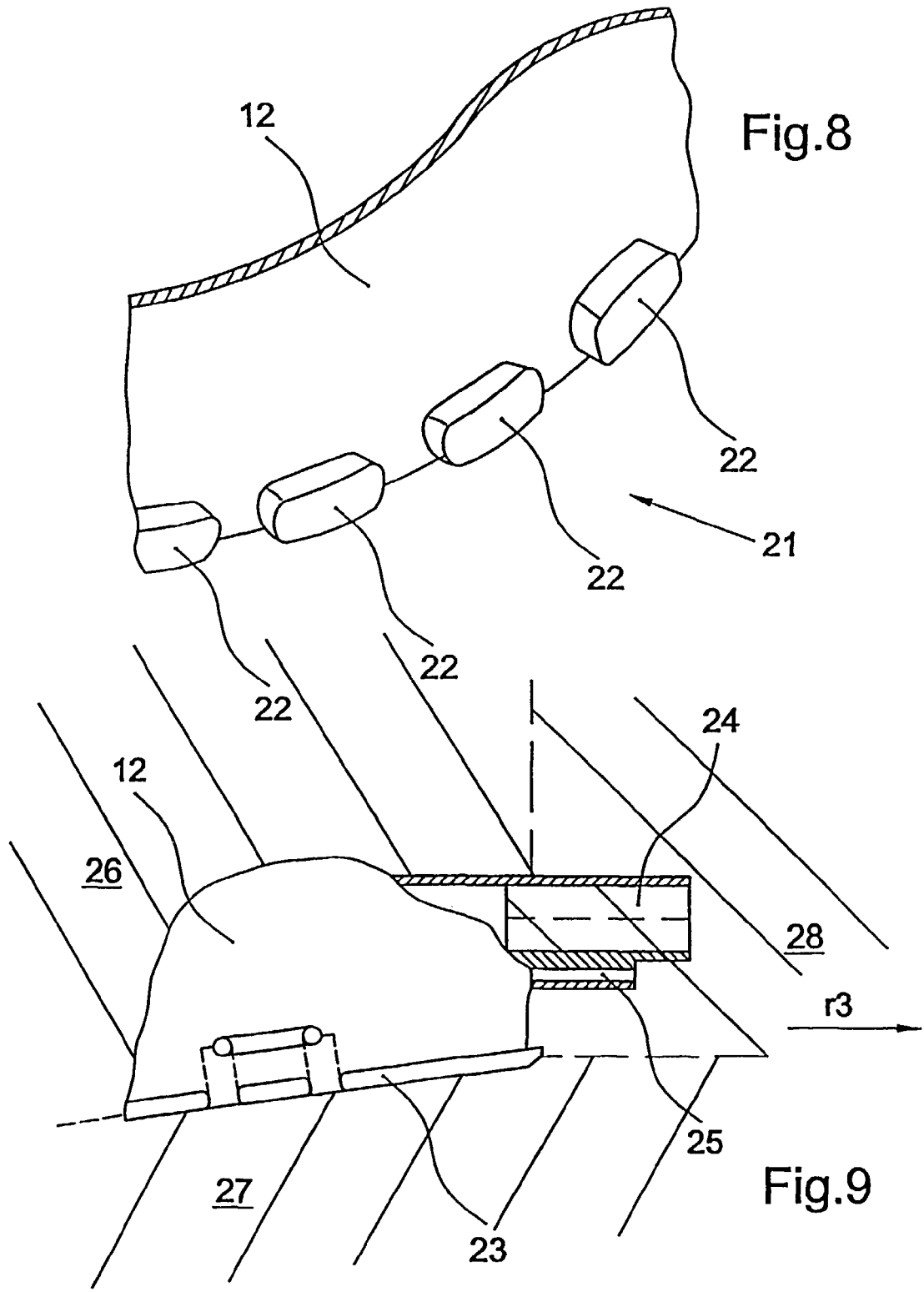

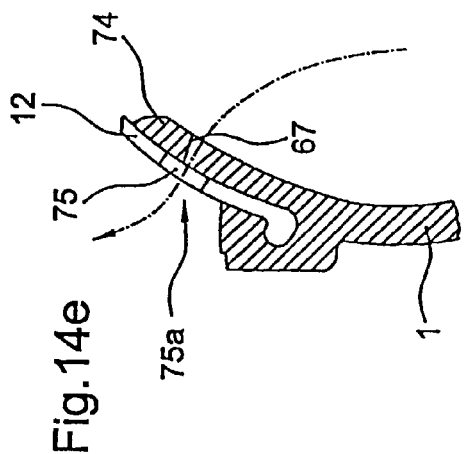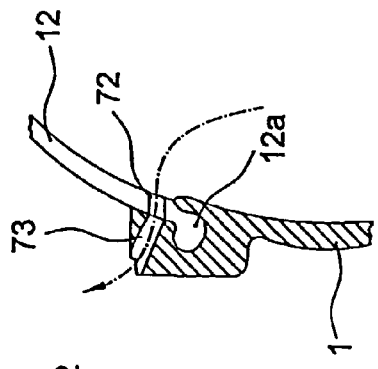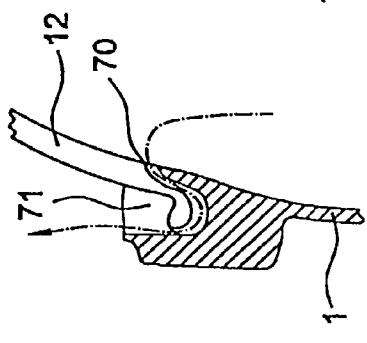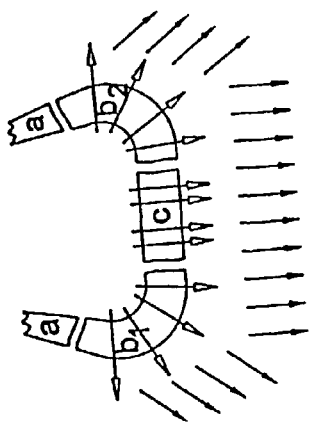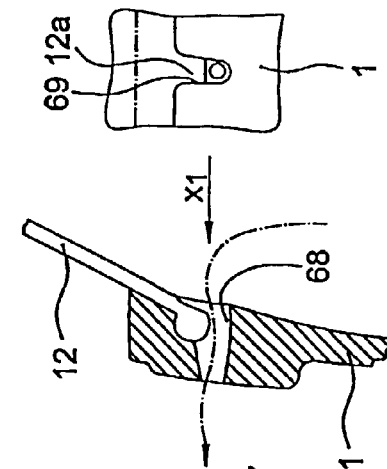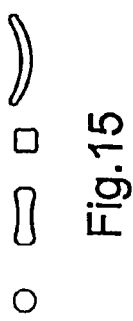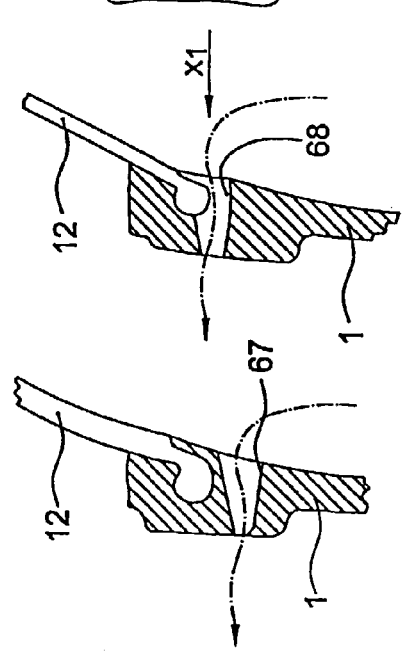

SEALING LIP DEVICE FOR A RESPIRATORY MASK, RESPIRATORY MASK AND A METHOD AND A MOULD FOR PRODUCING THE SAME

This application is the National Phase of International Application PCT/EP00/01586 filed Feb. 25, 2000 which designated the U.S. and that International Application was not published under PCT Article 21(2) in English.

The invention concerns a sealing lip device for a breathing mask, a breathing mask per se and a method and a mold for producing same.

In particular the invention concerns breathing masks which can be fitted to the nose region in sealing relationship and which have a sealing device extending in the region of the upper lip of the mask wearer between the mouth and the nose. Breathing masks are used in particular in the medical and technical areas for the feed of a respiratory gas, in particular under an increased pressure.

In those breathing masks, a seal in relation to the surface of the face of a wearer is usually achieved by a peripherally extending sealing lip made from an elastomeric material.

The sealing action achieved with a sealing lip of that kind generally increases with the pressure with which the sealing lip is pressed against the surface of the face. However the level of wearing comfort is adversely affected by comparatively high contact pressures. Depending on the respective sensitivity of the mask wearer long-term use of the known breathing masks gives rise to troubles.

The object of the present invention is to provide a breathing mask in which a high level of sealing action can be reliably achieved, with a high degree of wearing comfort.

In accordance with the invention that object is attained by a sealing lip device for a breathing mask having a receiving opening for receiving at least the nose tip region of a mask wearer, a sealing lip which is formed from an elastomeric material and which surrounds the receiving opening and which crosses the bridge of the nose in the application position and which has a contact zone provided for bearing against the face of a mask wearer, wherein the sealing lip is elastically yieldingly arranged in such a way that in the region of the bridge of the nose there is a higher degree of flexibility than in the region of the nostrils and/or the upper lip.

That advantageously affords a high degree of compatibility with the most widely varying facial architectures, with a high level of wearing comfort. The breathing mask according to the invention is distinguished in particular in the region of the bridge of the nose by a high degree of sealing integrity, without considerable pressures in relation to surface area occurring in that respect. The high level of sealing effect achieved in the region of the bridge of the nose effectively obviates in particular eye irritation effects and feeling the effects of drafts.

In accordance with a particularly preferred embodiment of the invention the defined flexibility of the sealing lip zone which fits on the region of the bridge of the nose is achieved by the sealing lip device being suspended in the region of that zone on a bellow structure. That bellows structure is preferably dimensioned in such a way that it forms an abutment device, upon suitably deep penetration of the bridge of the nose. The abutment surfaces which come into effect there are preferably such that they form a comparatively large contact area, at the latest in the inwardly resiliently deflected condition, so that even when the bellows structure becomes operative in the resiliently inwardly deflected condition, the arrangement does not involve any unacceptably high pressures in relation to surface area.

In a particularly advantage fashion, a hinge characteristic which is defined by different wall thicknesses is imparted to the bellows structure. Preferably the bend or hinge location is of a comparatively thin-gauge nature, whereas the zones which are disposed therebetween are slightly thicker. As an alternative thereto or also in combination with that measure, it is also possible to provide rolling bellows structures, by virtue of suitable wall thicknesses.

In a particularly advantageous manner the bellows structure has a plurality of fold indentations. Preferably at least one fold indentation extends from the region of the bridge of the nose into a region adjacent to the nostrils in the position of use of the mask.

Particularly when the structure has a plurality of fold indentations preferably at least one thereof extends around the entire periphery of the sealing lip device. The spring characteristic of the respective fold indentation can be definedly established for given peripheral zones in such a way that there is a higher level of flexibility in the region of the bridge of the nose and there is a lower level of flexibility in the region of the upper lip or in particular in the region of the nostrils. (Those orientations are with reference to the application position of the mask).

Particularly when using the bellows structure in the sealing zone region of the bridge of the nose, the sealing device is preferably designed in such a way that the flexibility of the sealing lip, which is in opposite relationship to the application direction, is so matched that there is an adaptation or articulation axis in the nostril or upper lip region. That makes it possible for the corresponding breathing mask to be fitted to the face of the mask wearer predominantly in the region of the zones of the face which are adjacent to the nostrils and on the upper lip, in which respect the preferably extremely thin-wall sealing lip zone which is provided for sealing at the bridge of the nose can be pivoted with respect to the mask frame, in accordance with the facial architecture. By virtue of the internal pressure obtaining in the mask, that pivotably supported sealing lip zone can then be uniformly pressed against the bridge of the nose of the wearer of the mask, without in that situation the occurrence of surface pressures which considerably exceed the internal pressure of the mask.

The particularly advantageous kinematics and hinge characteristic of the mask cushion or pad formed by the sealing lip device can in particular be achieved by local zones with a higher load-bearing capability being provided in the region of the sealing lip, which is adjacent to the nostrils or the upper lip.

In accordance with a particularly preferred embodiment of the invention the zones of higher load-bearing capability are formed by locally thickened zones of the sealing lip. The transition of the locally thickened zones is preferably effected along regions in the manner of the edge of a lens, or also in a shallowly terminating configuration, possibly without the transition between the zones being clearly perceptible.

In accordance with a particularly preferred embodiment of the invention the locally thickened zones are supported on a mask frame zone by way of a support structure which is formed in the sealing lip. That mask frame zone is preferably of a thick-wall nature and in that respect involves a wall thickness in the range of between 3 and 6 mm.

The zones of higher load-bearing capability are preferably of a pad-like nature, as is shown by way of example in FIG. 1 to which reference will be subsequently made in greater detail.

A form of support for the mask pad, which is particularly advantageous from ergonomic points of view is achieved if the zones of higher load-bearing capability, in the region of the face-contact zone, are each of a substantially crescent moon-shaped configuration. The limbs of those zones of higher load-bearing capability, which are provided in the region for bearing against the upper lip, are preferably of a shortened configuration in such a way that a zone of high elasticity and flexibility in opposite relationship to the application direction is provided in the region of the upper lip between the zones of higher load-bearing capability. That higher degree of flexibility can advantageously be achieved by also providing here a local fold structure or a correspondingly thin-walled zone.

In accordance with a particularly preferred embodiment of the invention the sealing lip device is mounted to a mask base body. The mask base body can also be formed from an elastomeric material, for example silicone rubber. In accordance with a particularly preferred embodiment of the invention however the mask base body is formed by a hard shell, for example comprising a fully transparent material. The hard shell preferably has a conduit connection facing in the application position towards the forehead region of the mask wearer. As an alternative thereto it is also possible for the hard shell to be provided with a central or lateral connecting structure for coupling a respiratory gas conduit.

Mounting the sealing lip device or the sealing pad to the hard shell or a mask base body is preferably effected by using a coupling structure. In accordance with a particularly preferred embodiment of the invention that coupling structure comprises, on the part of the hard shell, a peripheral bead portion and, on the part of the sealing lip device, a frame portion with a complementary receiving groove. The groove and the bead are preferably such that in the case of an expansion of the mask pad, caused by mask internal pressure, in the region of the coupling structure, there are surface pressures which are always higher than the internal pressure in the mask. That provides for a particularly reliable sealing action, without the addition of adhesives.

In a particularly advantageous fashion, there are provided means for fixing the position of the sealing lip device with respect to the hard shell in the peripheral direction. Those means can be formed for example by positioning projections or in particular by apertures in the peripheral bead.

A prestressing is preferably imparted to the sealing lip device, which prestressing is advantageously achieved by elastic deformation upon coupling to the hard shell. That makes it possible to definedly influence the deformation characteristics of the sealing lip device. In particular it is possible to prestress given zones of the sealing lip device in such a way that the formation of wrinkle folds in the region of the face-sealing zone is advantageously precluded.

In accordance with an advantageous embodiment of the invention the frame portion is such that it extends substantially in one plane. That permits the hard shell to be of a comparatively flat structure and allows the mask pad to be prestressed in a simple fashion.

As an alternative thereto however it is also possible for the mask arrangement to be designed in such a way that the frame portion is of a configuration which advances in the region of the articulation axis relative to the zone of high load-bearing capability. That makes it possible to already impart to the hard shell itself a configuration which substantially corresponds to the statistically most probable facial architecture.

Advantageously the wall thickness of the thin zone is in the range of between 0.65 and 1.85 mm. That wall thickness imparts to the mask a resistance to pressure which is sufficient even in the case of mask pressures in the region of 15 mbars.

The wall thickness of the zone of high load-bearing capability is preferably in the range of between 0.80 and 4 mm.

In accordance with a particularly preferred embodiment of the invention the mask pad is produced by a multi-stage mold cavity filling method. That makes it possible to impart to the zone of high load-bearing capability, a coloring which differs from the zone of low load-bearing capability. It is also possible to definedly match the mechanical properties of the materials respectively used for the respective zone.

The zone of high load-bearing capability is preferably formed by two elastomeric portions which project up from the lower corner region of the frame portion and which pass out into the sealing lip in the form of flat limbs. The sealing lip itself is preferably formed from an elastomeric material, in particular fully transparent silicone rubber. The outside surface of the mask pad, which comes directly into contact with the face of the mask wearer, is preferably of a velvety matte finish. That affords an improved feel when wearing the mask.

An embodiment of the invention which is particularly advantageous from manufacturing procedure points of view is afforded if the hard shell is injection molded to the sealing lip device. Besides particularly reliable coupling of the hard shell or the mask base body and the mask pad, that also precludes the formation of a gap, which is disadvantageous from bacteriological points of view.

In regard to a method of producing a sealing lip device for a breathing mask, the above-specified object is attained by an elastomeric material being introduced into a mold cavity formed by a mold, at least partially setting in the mold cavity, and being removed from the mold after opening thereof, wherein the elastomeric material is introduced into the corresponding mold cavity in two steps which occur in succession in time.

In that way it is possible to provide a mask pad which has a single sealing lip which in the application direction affords flexibility which is defined in accordance with the load-bearing capability and the statistically expected architectural variance of the corresponding zone of the face.

Advantageously, a carrier structure of the sealing lip device and a thin-wall zone of the sealing lip are formed in steps which are separate in terms of time, and possibly using materials involving different mechanical properties and possibly color.

Preferably the carrier structure is formed in a first injection step and the thin-wall zone is formed in a subsequent second injection step. The operation of introducing the respective material is preferably effected by injection or beforehand by suitably introducing same into the mold cavity to fill it.

The mold cavity which is provided for filling with the material forming the thin-wall zone is preferably defined by a mold which delimits the outside of a sealing lip being lifted off a core which delimits the inside of the sealing lip.

As an alternative thereto it is also possible for the carrier structure to be formed by a mold cavity which is defined by a core delimiting the inside of a sealing lip and an outer mold, wherein to form the thin-wall zone of the sealing lip the outer mold is changed and then the material for forming the thin zone is introduced into the mold cavity which is now present and which is intended for the thin-wall zone, and sets therein.

In the mold aspect of the invention, the above-specified object is attained by a mold for producing a sealing lip device for a breathing mask, comprising a mold core device which in conjunction with an outer mold defines a mold cavity having a fold portion.

It is advantageously possible in that way to produce the sealing lip device for example in the context of a fully automated silicone injection molding method.

In accordance with a particularly preferred embodiment of the invention the outer mold is of a multi-part nature. Preferably the outer mold comprises a mold half which delimits the outside surface of the sealing lip and a mold half which co-operates with said mold half and which delimits the rest of the region of the outside surface of the sealing pad. The inner region of the sealing pad is delimited by a preferably integral core device. With the described two-part embodiment of the outer mold, it is possible for an outer mold half to be withdrawn along a mold-opening axis which extends in a direction in opposite relationship to the side at the bridge of the nose or a direction remote from the upper lip sealing zone. The bellows zone which is locally provided in the region of the bridge of the nose and the mold-opening axis as well as the configuration of the coupling frame of the mask pad are preferably matched in such a way as to afford mold-opening angles at least in the region of 2°.

In particular in this case the outside of the sealing lip, which is towards the mask wearer, is preferably formed by an outer mold portion in conjunction with the mold core device, wherein the outer mold portion has a peripherally extending mold cavity channel which defines the outside of the sealing lip.

The outer separation edge of the mold cavity channel preferably extends in the region of the outer peripheral edge of the sealing lip. That advantageously avoids any burrs in the region of the face-contact surfaces.

In accordance with a particular aspect of the invention, an embodiment, which can be particularly advantageously implemented from production procedure points of view, of a leakage device for the discharge of at least partially consumed respiratory air into the ambient atmosphere is afforded by a breathing mask having a mask body and sealing pad device which is formed from an elastomeric material and which in conjunction with the mask body delimits a mask internal space and an outlet device for the discharge of at least partially consumed respiratory gas out of the mask internal space, wherein the outlet device has a flow path portion which is at least partially defined by the sealing pad device.

This measure can also be used independently of the above-described design configurations. Advantageous developments of this combination of the invention, which is independent per se, are set forth in the appendant claims.

Further advantageous configurations of the invention are recited in the appendant claims.

Figure 2:
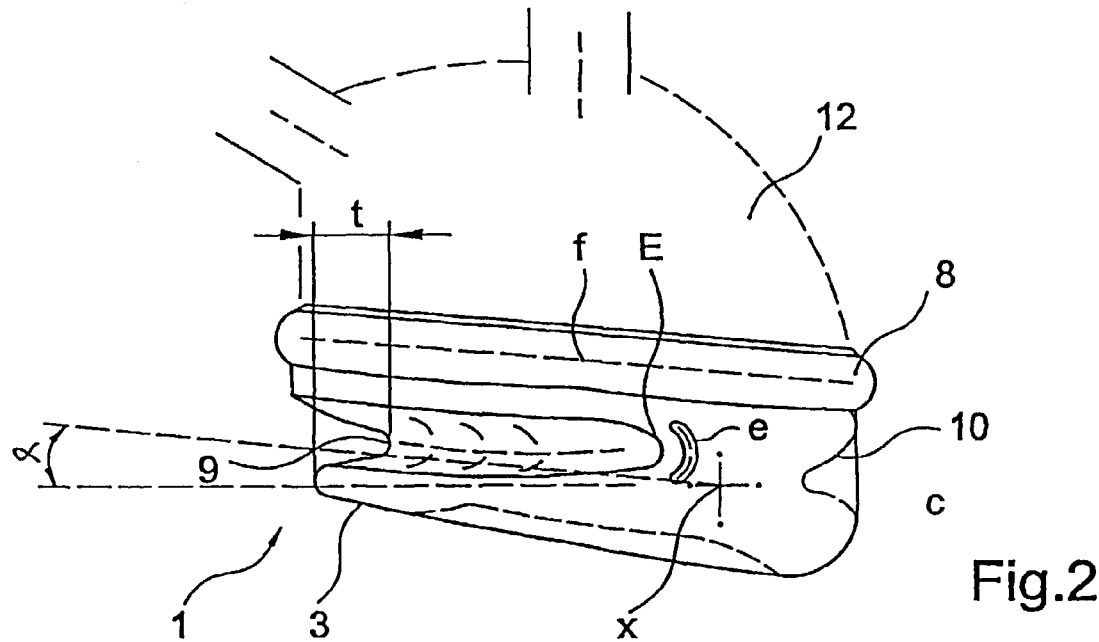
Figure 3A:
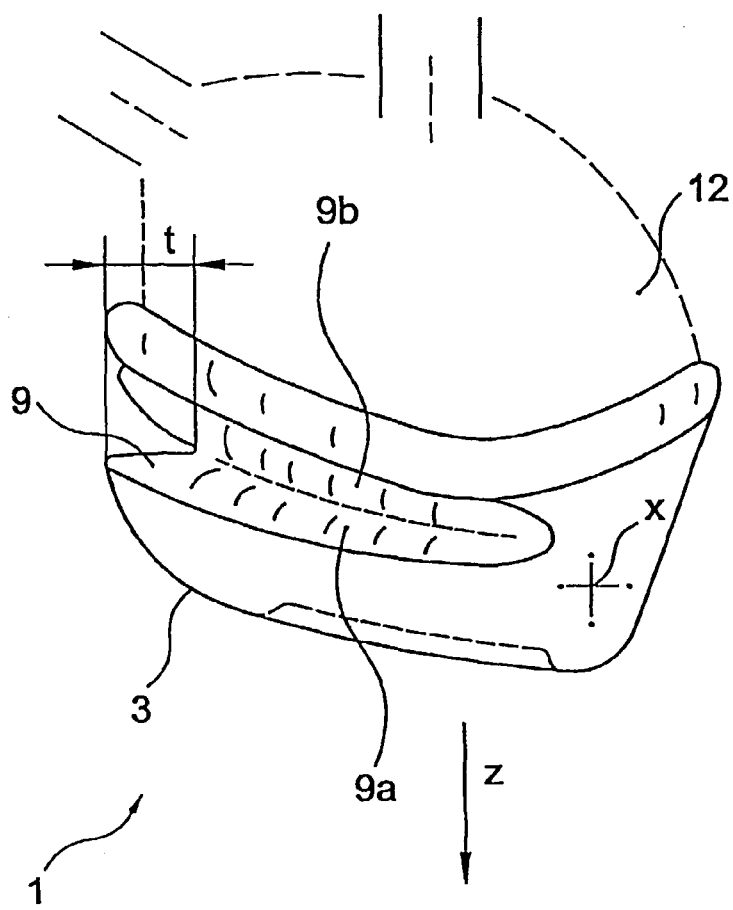
Figure 4:
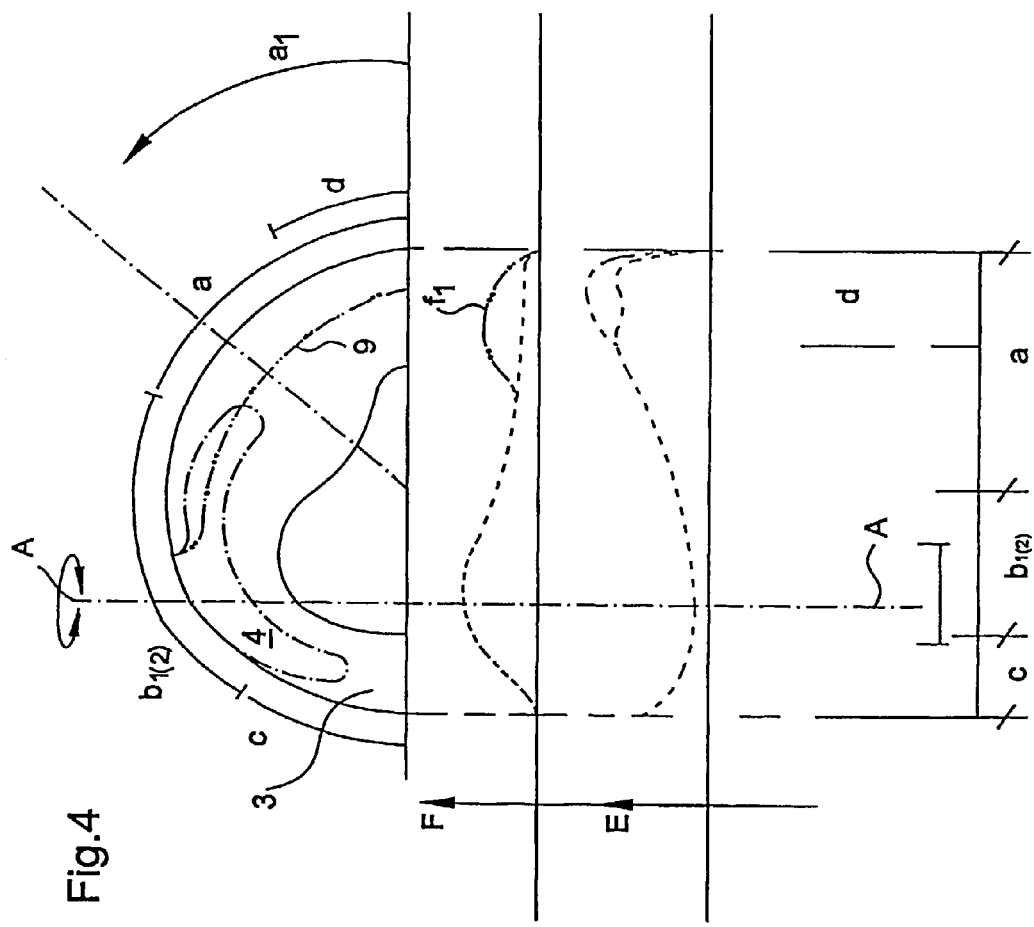
Figure 5:
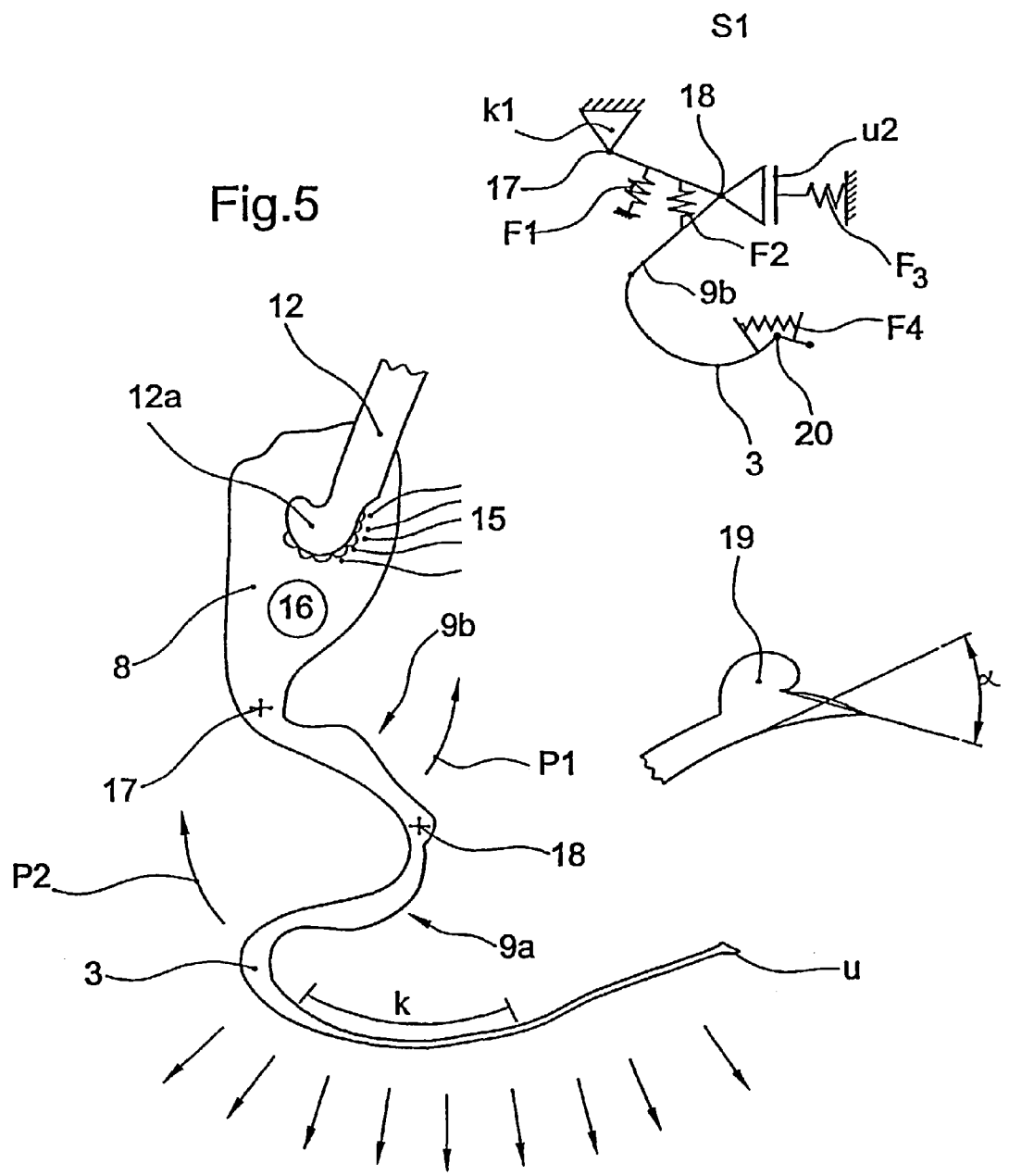
Figure 6:
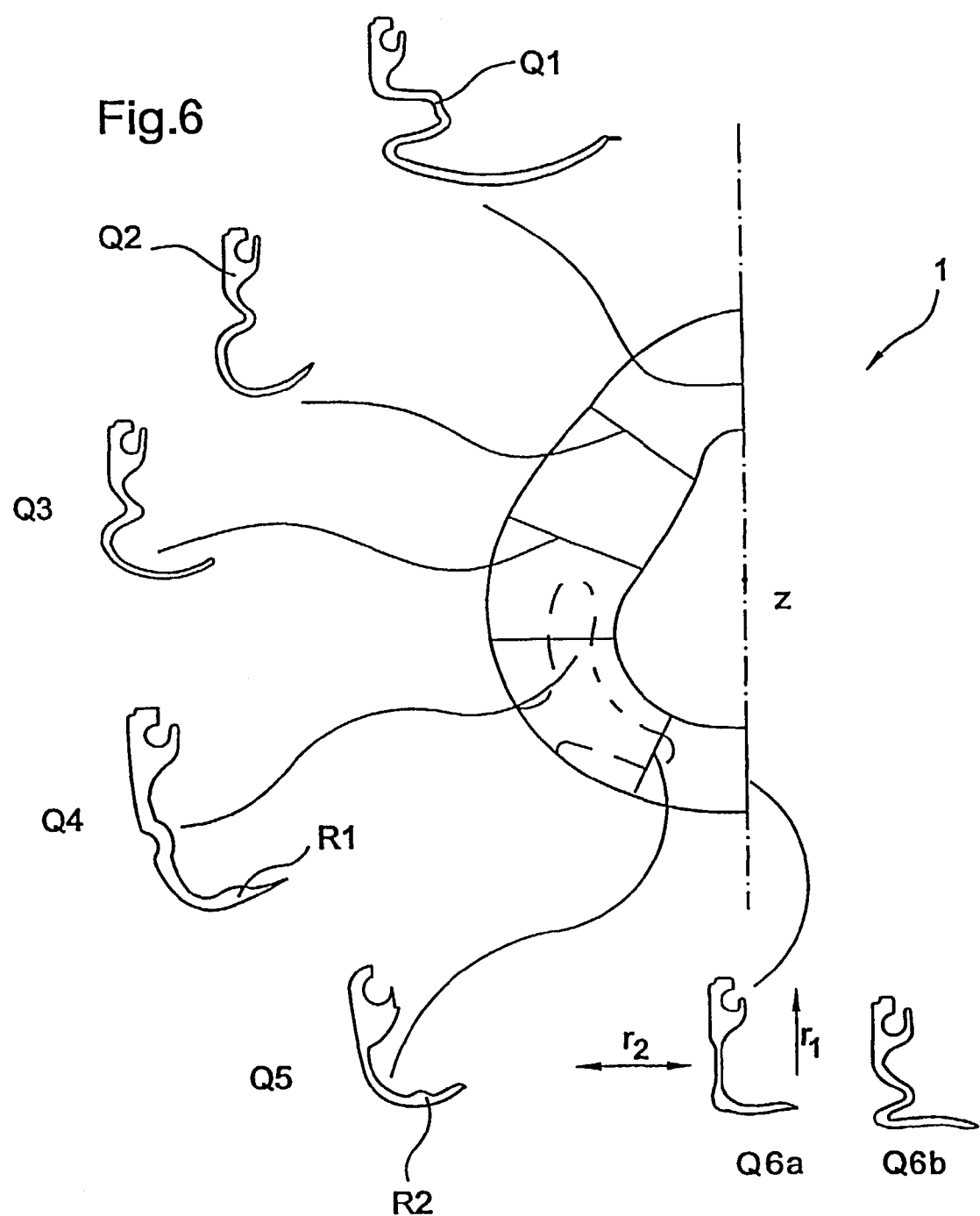
Figure 7:
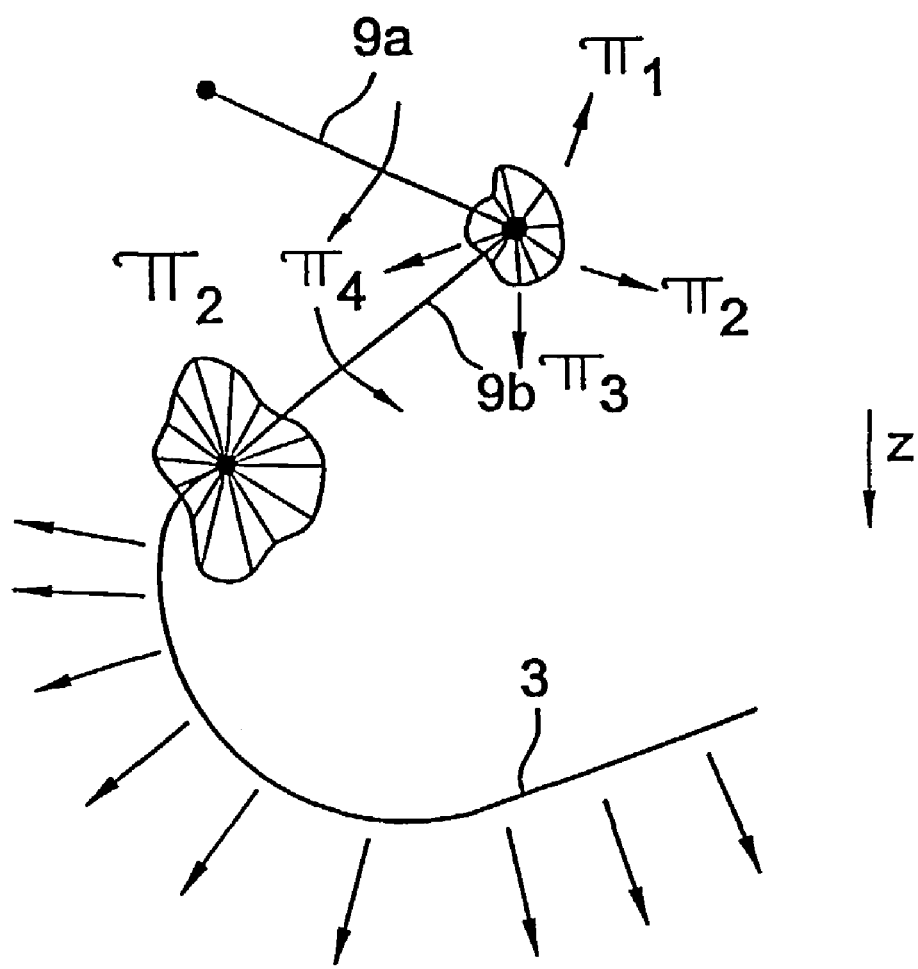
Figure 10:
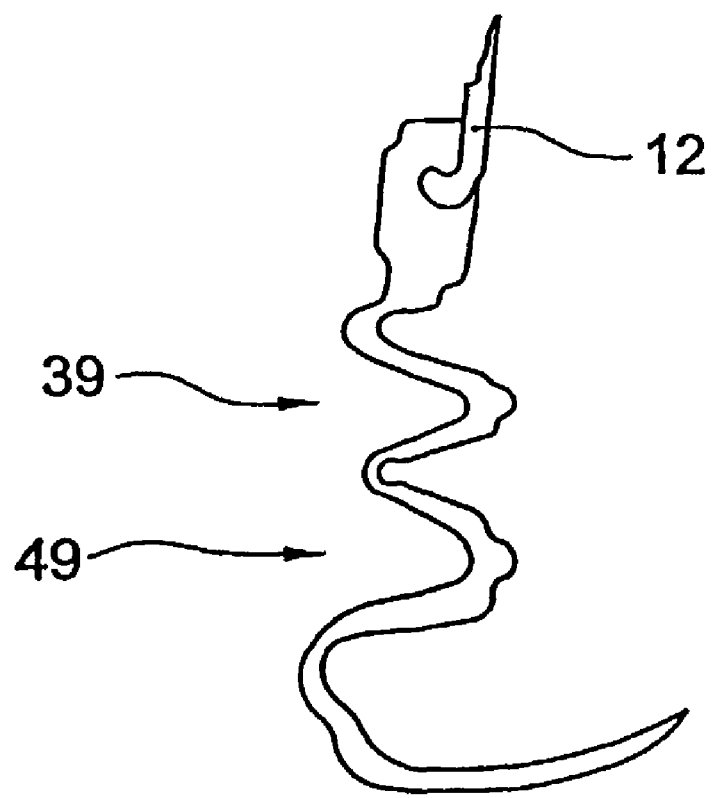
Figure 11:
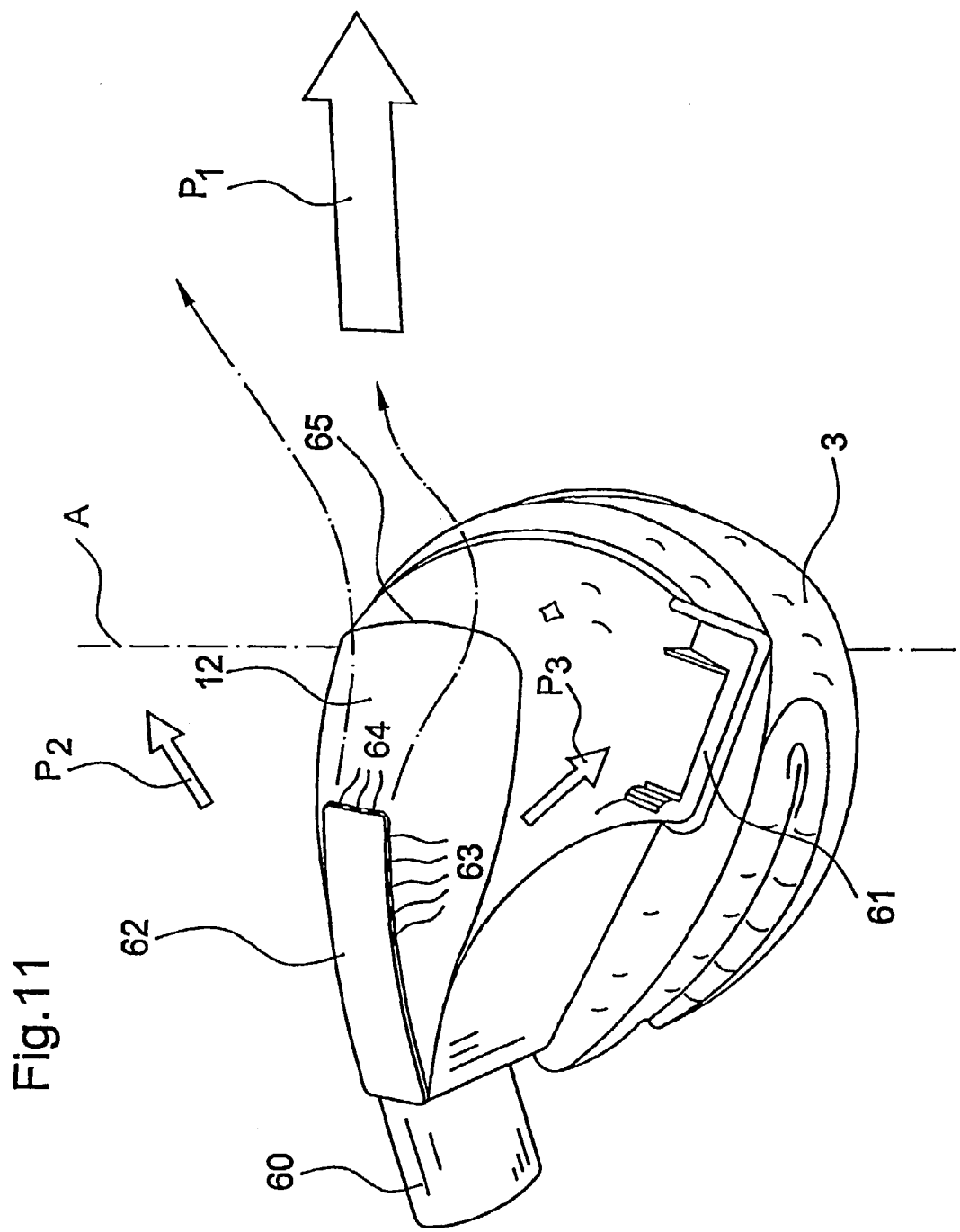
Figure 12:
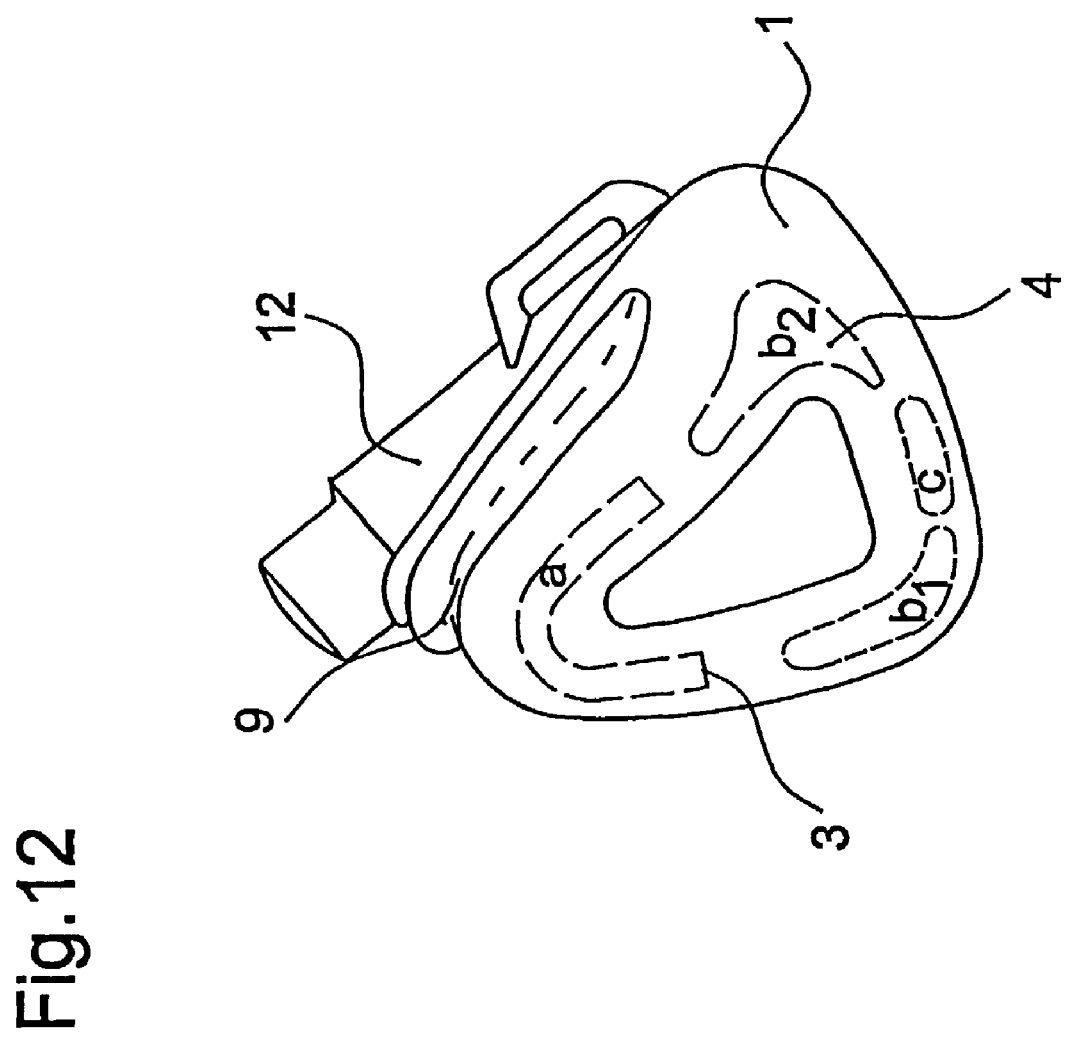
Figure 13:
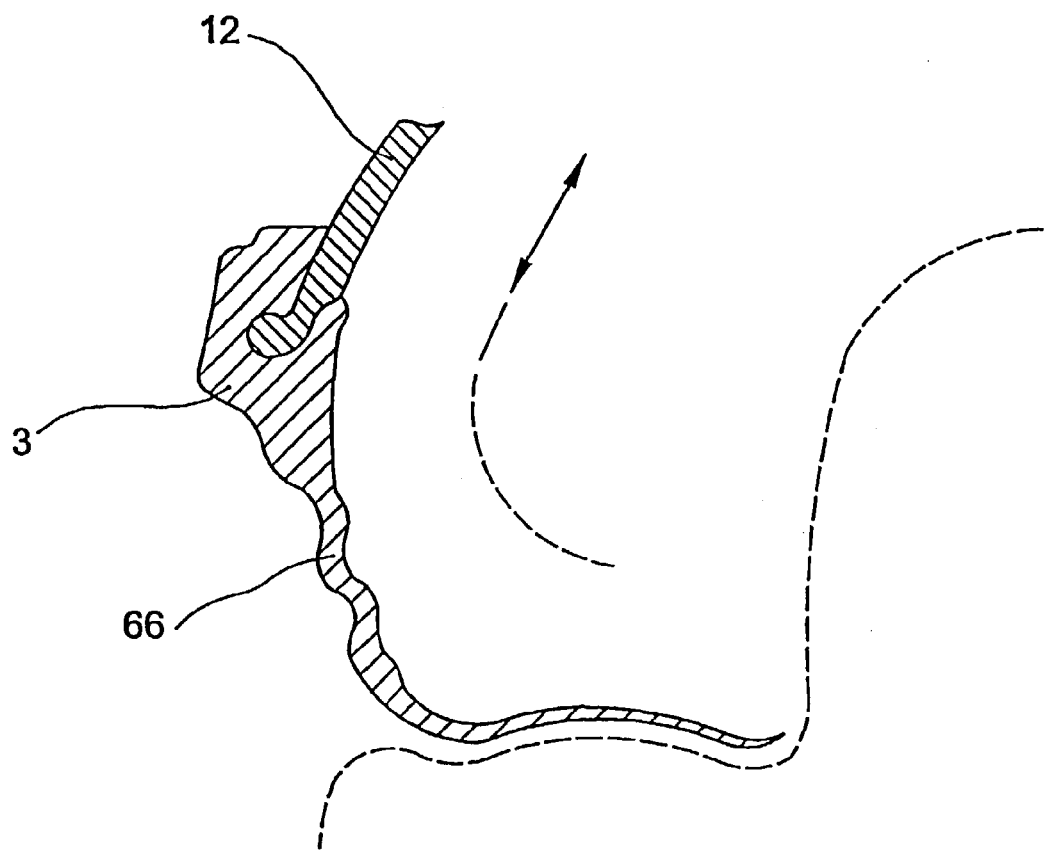

Further details of the invention will be apparent from the description hereinafter with reference to the drawing in which:

FIG. 1 shows a perspective view of a mask pad in accordance with a first embodiment of the invention with a local bellows structure and pad-like zones of increased load-bearing capability in the region of the sealing lips adjacent to the nostrils in the application position, together with associated sketches A1, A2 and A3 for illustration and accompanying explanation, FIG. 2 shows a simplified side view of a further breathing mask with a fold indentation and a frame portion extending substantially in one plane, FIG. 3a shows a simplified side view of a further embodiment of a mask pad, also with a bellows-like fold indentation and an indicated adaptation or articulation axis, FIG. 3b shows a simplified side view of a further embodiment of a breathing mask with a fold provided only in the rear third of the mask pad, FIG. 4 shows a simplified plan view of a sealing lip and diagrams for qualitative illustration of preferred matching of the load-bearing capability of the sealing lip, FIG. 5 shows a view in section to describe a preferred embodiment of a fold region with a hinge characteristic established by zones of differing wall thicknesses, including a diagrammatic sketch, FIG. 6 shows a diagrammatic view to describe preferred cross-sectional configurations in the case of a sealing lip device according to the invention, FIG. 7 shows a diagrammatic view to describe the flexibility of the hinge-like suspension for a sealing lip, FIG. 8 shows a diagrammatic view to describe a preferred measure for fixing the mask pad in the peripheral direction, FIG. 9 shows a further diagrammatic view to describe a preferred structure of a mold in conjunction with advantageous configurations of a mask base body (hard shell), FIG. 10 shows a simplified view in section to describe a fold portion with a plurality of fold indentations and a defined hinge characteristic, FIG. 11 shows a perspective view of a further preferred embodiment of a breathing mask with a mask sealing pad provided with a local bellows structure, FIG. 12 shows a perspective view of the breathing mask of FIG. 11 from below, FIG. 13 shows a simplified view in section through the sealing device which is disposed on the upper lip, to describe the substantially smooth-wall transition of the sealing lip into the hard shell mask body, FIG. 14a shows a simplified view in section through a sealing lip with integrated leakage opening, FIG. 14b shows a simplified view in section through a sealing lip with integrated leakage opening, but with a flow path partially delimited by the mask frame, FIG. 14c shows a simplified view in section through a sealing lip with integrated leakage opening, with a flow path which is formed in the mask frame and which passes into the sealing lip frame portion, FIG. 14d shows a simplified view in section through a sealing lip with integrated leakage opening, but with mutually aligned passages in the hard shell and the sealing lip device, FIG. 14e shows a simplified view in section through a sealing lip with integrated leakage opening, but with a portion which is extended upwardly in a bib-like configuration from the interior to a through opening, and with a through opening formed therein, FIG. 15 shows simplified diagrammatic views of preferred cross-sections of the flow paths, and FIG. 16 shows a simplified diagrammatic view in principle to describe preferred leakage zones.

The sealing lip device which is shown in FIG. 1 and which is in the form of a mask cushion or pad 1 is made from an elastomeric material, here transparent silicone rubber.

The mask pad 1 includes a sealing lip 3 which extends around the nose receiving opening 2. The sealing lip 3 has an outer surface which is curved convexly in the embodiment illustrated here.

The sealing lip 3 is of such an arrangement and configuration that it has, of itself, zones of differing load-bearing capability. In the embodiment illustrated here that is achieved by suspension, which is flexible in opposite relationship to the application direction Z, of the sealing lip zone a provided for bearing against the bridge of the nose (see sketch K1).

In addition thereto, in the region of the zone b1, b2 (sketch K1) adjacent to the nostrils, the sealing lip 3 is of such a configuration that here it is of a higher load-bearing capability. That provides for pivotability of the mask pad about an adaptation axis X, which extends transversely through the mask pad in the region identified in sketch K1 by the letter e.

The higher load-bearing capability is achieved here by zones 4 which are thickened in a pad-like manner and which here advantageously run into the sealing lip 3 in a crescent moon-like configuration. The zones 4 of higher load-bearing capability are respectively supported at a support wall portion 5 which is also comparatively thick-walled. The support wall portions 5 also form an integral component part of the mask pad 1 and are embodied in the form of thick-wall zones of the front peripheral wall which extends in the zones b1, c and b2.

The degree of flexibility in opposite relationship to the application direction decreases along the sealing lip 3, starting from the zones 4 of high load-bearing capability, to the zenith Q at the side at the bridge of the nose, and then slowly rises to the outer edge point R.

In the illustrated embodiment, the mounting of the zone a of the sealing lip 3, which is yielding in opposite relationship to the application direction Z, is achieved by means of a folding bellows structure of differing load-bearing capability.

The differing load-bearing capability is achieved here both by the geometry and arrangement of the bellows structure and also by a particular wall thickness configuration. That wall thickness configuration will be discussed in greater detail hereinafter in particular with reference to FIGS. 5 and 6.

The mask pad 1 further includes a peripherally extending frame 8 provided with a fixing profile means which is of a complementary configuration to a fixing profile portion provided on a mask base body (not shown).

The peripheral length of the frame 8 and the configuration thereof around a central axis z of the mask pad 1 are selected in such a way that, in conjunction with a mask base body, the arrangement provides for defined prestressing of the mask pad 1, in particular a tendency towards forward curvature in an outward direction.

In the illustrated embodiment the wall thickness of the sealing lip 3 is in the range of between 0.6 and 3.2 mm.

The configuration of the peripheral edge u which borders the nose receiving opening 2 is selected in such a way that there are formed two segments s1, s2 (sketch K3) which project inwardly slightly relative to the axis z of the mask.

By virtue of the configuration of the peripheral edge u being matched to the convex curvature of the sealing lip 3, it is possible to achieve a deformation characteristic with which an expansion of the sealing lip 3 in the region of the peripheral edge results in a definedly increased surface pressure against the face of the wearer of the mask.

Provided in a front end center region c is a further zone of reduced load-bearing capability. That definedly reduced load-bearing capability is afforded here by a markedly reduced wall thickness. It is also possible to provide local folding bellows structures or rolling bellows structures in the zone c.

A particularly preferred embodiment of a sealing lip device is afforded by virtue of the fact that integrated into same are outlet openings 50, by way of which a defined flow of gas can flow away out of the interior of the breathing mask. Those outlet openings are preferably of an outwardly conically tapering cross-section, as shown in sketch K2.

Preferably, those outlet openings are initially closed for example by a thin film and are then opened as required for example by puncturing with a needle. As can further be seen from this sketch the mask pad 1 can be mounted to a mask base body 12 by way of a frame portion 8. For that purpose the arrangement preferably has a peripheral bead structure of a crochet needle-like cross-section and with rounded edges.

FIG. 2 shows a side view of a further embodiment of a mask pad 1. In this embodiment the frame 8 extends substantially in a flat frame-defining plane f.

The mask pad 1 also has in the sealing region of the bridge of the nose a local folding bellows structure 9 which provides for flexible suspension of the sealing lip 3.

A fold indentation 10 is also provided in the front region c (definition similarly to the sketch K1 in FIG. 1). The arrangement afforded in that way defines an adaptation and articulation axis X or an instantaneous center of rotation about which the sealing lip 3 can be elastically tilted. The arrangement here is such that tilt angles α in a range of up to 15° are possible. Besides the tilting movement itself the sealing lip 3 can also experience individual deformation, corresponding to the facial architecture. In particular the peripheral edge u of the nose receiving opening is stretched.

When relatively large tilt angles are involved, here the bellows structure becomes effective as an abutment device and limits in an also elastically yielding manner further engagement of the bridge of the nose into the mask pad 1.

The bellows structure 9 has the greatest indentation depth t in the region of the end which is towards the bridge of the nose. That indentation depth t gradually decreases to the front end E of the bellows structure 9.

In the embodiment illustrated here, the end of the bellows structure 9 is of a rounded configuration. Advantageously, provided in the region of the front end E of the fold indentation is a microfold structure e which provides for a more uniform reduction in stresses in the material in that region. That affords improved durability.

FIG. 3a shows a further embodiment of a mask pad 1 in conjunction with a mask body 12 which is only indicated.

This embodiment also has a local folding bellows structure 9. The geometry of this bellows structure 9 is so selected that the fold flanks 9a, 9b extend inclinedly relative to each other. Overall in this case also the indentation depth t in the region of the end towards the bridge of the nose is larger than in the other regions. The mask pad 1 also defines an adaptation axis X which extends in the region of the zones c1, b2 and c at the level of the nostrils of the wearer of the mask.

The mask pad 1 also has a higher degree of flexibility in opposite relationship to the application direction Z by virtue of the suspension arrangement provided here for suspending the sealing lip 3 at a local bellows structure 9, in the region of the zone a which seals off the bridge of the nose.

FIG. 3b shows a further view of a breathing mask with a mask pad 1 according to the invention. The mask pad 1 is here fixed by way of a frame 8 to a mask base body 12. A bellows structure 9 is provided here in the region of the portion of the sealing lip 3 which seals off the bridge of the nose. In a departure from the above-described embodiments in this case also the peripheral wall of the mask pad is also of thin-wall configuration in the region of the bellows structure 9. The mask pad 1 is stretched onto the mask base body 12 with considerable expansion and stretching of the frame 8.

FIG. 4, in conjunction with a plan view onto a half of the sealing lip 3, illustrates the load-bearing capability and the flexibility of the mask pad 1.

The lowest level of flexibility E of the mask pad 1 obtains in the region b. The highest level of flexibility obtains in the region a which covers over the bridge of the nose and the upper side flanks of the nose of the mask wearer. Obtaining in the region c in addition to the flexibility in opposite relationship to the application direction Z there is also a relatively high level of flexibility in the radial direction.

The adaptation axis A extends through the zone b of relatively high load-bearing capability. When a predetermined depth of penetration into the mask pad 1 is exceeded, the bellows structure becomes operative in a region d as an abutment device and in that case causes a rapid rise in the pressure force F transmitted by way of the sealing lip 3, as is indicated by the dash-dotted line portion f1.

The particular mechanical properties of the suspension arrangement for the sealing lip 3 are preferably determined by the wall thickness in the region of the bellows structure 9 and by the indentation depth and the orientation of the bellows flanks 9a, 9b (FIG. 3a).

FIG. 5 shows a preferred configuration of the wall thicknesses of the bellows structure 9. The mask pad 1 is fixed to a mask base body 12 in this case by way of a rounded profile structure 12a which extends along the frame 8. In the illustrated embodiment that profile structure 12a is of a crochet needle-like cross-section. Provided at least in a portion-wise manner in the region of the contact zone between the frame 8 and the mask base body 12 are peripherally extending profile legs 15 which, even in the case of a considerable relative movement, provide a secure sealing action.

Beneath the frame 8 there is initially a thick-wall portion 16 which gradually reduces to a first bellows hinge location 17. That bellows hinge location 17 is adjoined by a first bellows flank limb 9b. That bellows flank limb 9b has in cross-section zones of differing wall thickness and extends to a bellows inner hinge location 18 defined by a thin-walled zone.

The bellows inner hinge location 18 is in turn adjoined by a second bellows flank limb 9a which also has zones of differing wall thickness.

Finally, the sealing lip 3 is suspended on the second bellows flank limb 9a. The sealing lip 3 is here extremely thin-walled in comparison with the bellows structure 9.

The sealing pad cross-section illustrated here corresponds in qualitative terms to the sealing pad cross-section in the region of the zone identified as a1 in FIG. 4.

In the course of applying the mask pad to the face of a mask wearer, the sealing lip 3 firstly bears against the face. The bellows flank limbs 9a, 9b are then deflected resiliently inwardly, corresponding to the depth of engagement of the bridge of the nose, as illustrated by the arrows P1 and P2. In the case of particularly deep engagement of the bridge of the nose the inner surface of the sealing lip 3 possibly comes into contract in the region of the zone k with the inside surface, which faces theretowards, of the bellows flank limb 9b. The bellows flank limb 9b in turn can bear on the outside surface, which faces theretowards, of the bellows flank limb 9a.

The kinematics of the sealing pad suspension configuration will be clear by reference to the accompanying functional sketch S1. Thus the frame can be viewed as a fixed suspension means K1 at which the bellows flank limb 9b is mounted pivotably at the hinge location 17. The inherent elasticity of the elastomeric material in the region of the hinge location 17 is symbolically indicated by the spring F1.

The bellows inner hinge location 18 also involves an inherently elastic characteristic which is indicated by the spring F2. The loose mounting K2 and the spring F3 are due to the fact that this involves a spatial, ring-like structure which also carries forces in the radial direction.

The hinge location 18 is adjoined by the bellows flank limb 9b and same is adjoined by the diaphragm-like sealing lip 3.

Provided along the inner peripheral edge u is a microsealing lip structure by which a sealing edge which terminates in a thin configuration is slightly prestressed outwardly. The microsealing lip structure has a bead portion 19 which increases the resistance to tearing of the sealing lip 3.

The mechanics of this microsealing lip structure is indicated in sketch S1 by a spring F4 and a hinge location 20. The sealing lip which is elastically suspended in that way, as indicated by the small arrows, can be urged flexibly against the surface of the face of the mask wearer, as a consequence of the internal pressure obtaining in the interior of the mask.

As can be seen from FIG. 6 the mask pad 1 is preferably of differing cross-sections along its configuration around the axis Z of the mask, as is diagrammatically indicated here.

The cross-section Q1 has a marked hinge characteristic with abutment properties.

The cross-section Q2 already has a lower hinge characteristic and a smaller fold indentation.

In the region of the cross-sections Q3, Q4 the bellows property decreases still further.

The higher load-bearing capability of the cross-sections Q4 and Q5 is achieved by local thickenings R1, R2 which extend lens-like into the sealing lip. In the zones of high load-bearing capability, it is possible to forego the bellows structure, as has happened here.

The cross-sections Q6a or Q6b are such that there is flexibility in the directions r1 and r2 indicated here. That affords improved adaptability, in terms of the upper lip architecture, immediately beside the load-bearing zones.

It is also possible for the bellows structure 9 to be of a thin-wall nature. The kinematics of a structure of that kind is diagrammatically shown in FIG. 7. The diaphragm-like sealing lip 3 is here suspended on two limbs (bellows flank limb 9a, 9b). This embodiment, even with low internal pressures in the mask, guarantees a high level of adaptability. The elasticity characteristics are illustrated, with reference to a unit force, for all loading angles, by the polar diagrams I11, 112 which are diagrammatically shown here. As can be seen, a defined degree of adaptability is afforded by the suspension arrangement according to the invention for the sealing lip 3, not only in opposite relationship to the application direction Z but also in all other directions. The location vectors t1, n2, n3 and n4 clearly show that flexibility in the region of the bellows inner hinge location. The mobility options of the bellows inner hinge location 18 are also transmitted (under the influence of the mask pad peripheral forces) to the suspension region of the sealing lip 3.

FIG. 8 diagrammatically shows a profile structure 21 which is provided in respect of a mask base body 12 and which advantageously provides for reliable fixing of the mask pad in the peripheral direction. The illustrated embodiment for that purpose has a plurality of individual fixing projections 22 along the periphery of the mask base body 12. As an alternative thereto or also in combination with that measure, it is also possible to provide further fixing means, in particular peg-like projections.

FIG. 9 shows in greatly simplified form the structure of a mold for producing the mask base body 12. By virtue of the aperture in the peripheral bead 23 in the region of the respective strap loops, it is possible for the strap loops to be injection molded integrally with the mask base body 12, without the need for sliding mold portions in that respect.

In the embodiment of the mask base body 12 diagrammatically illustrated here, provided in parallel with a respiratory gas passage 24 is a secondary passage 25 by way of which for example pressure measurement can be effected, without reductions in cross-section occurring in that case.

The tool here is of a three-part construction and includes an upper mold half 26, a lower mold half 27 and a sliding mold portion 28 which can be withdrawn in the direction r3 from the respiratory gas passage 24.

Although the invention has been described hereinbefore with reference to preferred embodiments in which there is a single fold indentation which does not extend around the entire periphery of the mask pad, the invention is not limited to embodiments of that kind.

For example it is possible for the bellows structure to be provided with a plurality of fold indentations, of which possibly one or more extend around the entire periphery of the mask pad.

An example of a corresponding cross-sectional configuration is shown in FIG. 10. The mask pad 1 which is here fixed to a mask base body 12 which is only indicated in respect of a portion thereof, by way of a peripheral bead structure of a crochet needle-like cross-section, has two local fold indentations 39, 49. The wall of those local fold indentations 39, 49 is matched in regard to a defined hinge and flexibility characteristic.

In this embodiment the sealing lip 3 is of a comparatively thick-wall nature. That cross-section is suitable in particular for silicone rubber material with an extremely low Shore hardness.

The breathing mask shown in FIG. 11 includes a mask base body 12 which is made from a preferably fully transparent thermoplastic material. Provided in a wall portion which in the application position of the mask is adjacent to the forehead region of the mask wearer is a connecting portion 60 which here is of a polygonal cross-section.

The sealing pad device 3 is fixed to the mask base body 12 by way of a peripheral bead structure (not visible here). The sealing pad device 3 has a bellows structure which extends locally from the upper end region to an adaptation axis A. Provided in the region of the adaptation axis A on both sides of the sealing pad are zones of higher load-bearing capability which are formed by thicker-walled, spherically curved zones of the sealing pad device.

For the purposes of fitting the breathing mask to the face of a mask wearer, provided at both sides of the mask are fixing devices 61, by way of which a head band can be coupled to the breathing mask.

On its top side the mask body 12 is provided with a projection 62 by which the mask body generally is stiffened, thereby affording an improved characteristic in terms of sound conduction through solids.

Also provided in the region of the top side of the mask body 12 are a plurality of outlet openings 63, 64, by way of which a low-noise, directed discharge flow of partially consumed respiratory air can occur from the interior of the mask. The discharge of that leakage gas flow is promoted by a breakaway edge 65 of a spoiler-like configuration. The openings 64 direct the flow substantially in the direction indicated by the arrow P1. The openings 63 which are also provided on the opposite side (not visible here) of the projection 62 open in the directions P2 and P3.

FIG. 12 shows the breathing mask of FIG. 11 from a direction of view which is directed inclinedly from below onto the zone 4 of high load-bearing capability. It is also possible to see here, beside the local bellows structure 9, the region of the sealing lip 3 which bears against the face of the mask wearer. In the region of the zone a the mask is distinguished by a high level of adaptability to different nose bridge heights. In the zones b1 and b2 the mask pad 1 is supported in a defined manner against the face of the mask wearer. In the region c once again there is a higher level of flexibility and a higher degree of adaptability to different upper lip contours.

The mask pad is of such a design configuration that there is a relief of load in the region of the zones b1 and b2, as a consequence of the internal pressure in the mask which occurs in the context of over-pressure artificial respiration. The surface pressure of the mask pad in the region of the zones a and c is substantially determined by the internal pressure in the mask. In the peripheral direction the sealing pad 1 has a high level of radial stiffness whereby the tendency to oscillation of the sealing pad in relation to alternating artificial respiration pressures is markedly reduced.

FIG. 13 is a greatly simplified view in section through the region of the sealing lip device 3, which fits on the upper lip 70 of a mask wearer. In a transitional region from the sealing pad device into the hard shell body 12, the configuration of the cross-sections of the sealing pad device 3 and the hard shell body 12 is such that there is a substantially smooth transition in respect of the respective internal surfaces. That ensures a favorable flow path directly in the region of the nostrils of the mask wearer.

As indicated, in this case also there is a local bellows structure 66 which ensures improved adaptability to different upper lip architectures.

FIG. 14a shows a portion of the arrangement illustrating the transitional region between the hard shell body 12 and the sealing pad device 1. Formed directly in the sealing pad device 1 is a leakage opening 67 which is here of a cross-section which decreases in the discharge direction. The cross-sections of that leakage opening 67 are preferably of the configuration diagrammatically shown in FIG. 15.

FIG. 14b shows a further embodiment of a leakage opening 68 which is integrated into the sealing pad device 1. In the embodiment illustrated here a wall formed by the hard shell body 12 extends into the flow path. This embodiment can be cleaned in a particularly advantageous manner as the flow path is exposed over a large area after removal of the sealing pad device 1 from the hard shell body 12. Illustrated in the sketch shown immediately therebeside is a view of a detail of that sealing pad, in the direction of view identified as x1. As can be seen therein the peripheral bead 12a of the hard shell body 12 extends partially into the recess 69 formed in the cushion pad device 1.

In the embodiment shown in FIG. 14c, provided in the region of the join between the hard shell body 12 and the sealing pad device 1 in the hard shell body is a channel portion 70 by way of which there can be a discharge flow of gas, as indicated by dash-dotted lines. The exit region of the channel portion 70, as illustrated, opens into a outlet passage 71 which is defined jointly by the sealing pad device 3 and the hard shell body 12.

In the embodiment shown in FIG. 14d, provided in the hard shell body 12 is at least one outlet passage 72 which goes into an aligned discharge passage 73 in the sealing device 1.

FIG. 14e shows an embodiment of a leakage device in which a wall portion 74 which is integral with the sealing pad device 1 is taken from the interior to an outlet opening region 75 of the hard shell body 12. That wall portion 74 is here provided with an outlet opening 67 which tapers conically in the discharge direction and which is arranged coaxially with respect to a preferably considerably larger outlet opening 75a.

The flow paths described with reference to FIGS. 14a through 14e are preferably of at least one of the cross-sections diagrammatically shown in FIG. 15.

FIG. 16 indicates a preferred location for providing the discharge flow openings which are provided jointly with the sealing pad device 1 or also separately therefrom. Preferably the discharge flow occurs in the region of the zone c in combination with the zones b1 and b2, but preferably larger volume flows are admitted in the region c.

The invention claimed is:

1. A sealing lip device for a breathing mask having a receiving opening for receiving at least the nose tip region of a mask wearer, a sealing lip which is formed from an elastomeric material and which surrounds the receiving opening and which is configured to cross the bridge of the nose and which has a contact zone provided for bearing against the face of a mask wearer in use, wherein the sealing lip is elastically and yieldingly arranged in such a way that a first sealing lip zone which in use seals the region of the bridge of the nose has a higher degree of flexibility than a second sealing lip zone which in use is adjacent to at least one of the nostrils and the upper lip of the mask wearer in the application position of the breathing mask, wherein the sealing lip is suspended on a folding bellows structure in the region of the first sealing lip zone provided for sealing of the region of the bridge of the nose, the folding bellows structure including a fold indentation having zones of differing wall thickness, wherein a wall thickness of a zone of high load-bearing capacity is in the range of between 0.80 and 4 mm, and wherein the zone of high load-bearing capability is formed by two elastomeric portions which project up from a lower corner region of a frame portion and which extend into the sealing lip in the form of flat limbs.

2. A sealing lip device as set forth in claim 1, wherein the bellows structure forms an abutment device.

3. A sealing lip device as set forth in claim 1, wherein the bellows structure has a hinge characteristic defined by different wall thicknesses.

4. A sealing lip device as set forth in claim 1, wherein the bellows structure has a plurality of fold indentations.

5. A sealing lip device as set forth in claim 1, wherein at least one fold indentation is structured to extend from the nose bridge region into a region adjacent to the nostrils in the position of use of the mask.

6. A sealing lip device as set forth in claim 1, wherein at least one fold indentation extends around the entire periphery of the sealing lip device.

7. A sealing lip device as set forth in claim 1, wherein the flexibility of the sealing lip, which is related to an application direction, is structured to define an articulation axis in the nostril or upper lip region in use.

8. A sealing lip device as set forth in claim 1, wherein zones of higher load-bearing capability are provided in the region of the sealing lip and are configured in use to be positioned adjacent to the nostrils or the upper lip.

9. A sealing lip device as set forth in claim 8, wherein the zones of higher load-bearing capability are formed by locally thickened zones of the sealing lip.

10. A sealing lip device as set forth in claim 9, wherein the locally thickened zones are supported on a mask frame zone by way of a support structure which is formed in the sealing lip.

11. A sealing lip device as set forth in claim 8, wherein the zones of higher load-bearing capability are of a pad-like configuration.

12. A sealing lip device as set forth in claim 8, wherein the zones of higher load-bearing capability are each of a substantially crescent moon-shaped configuration in the region of the face-contact zone.

13. A sealing lip device as set forth in claim 8, wherein a zone of high flexibility in and in opposite relationship to an application direction is provided in the region of the upper lip in use in a region which is between the zones of higher load-bearing capability.

14. A sealing lip device as set forth in claim 1, wherein the sealing lip device is adapted to be mounted to a mask base body.

15. A sealing lip device as set forth in claim 14, wherein the mask base body is formed by a hard shell.

16. A sealing lip device as set forth in claim 15, wherein the hard shell has a conduit connection which faces towards a forehead region in use.

17. A sealing lip device as set forth in claim 1, further comprising a coupling structure for coupling the sealing lip device to a hard shell.

18. A sealing lip device as set forth in claim 15, further comprising structure to fix the position of the sealing lip device with respect to the hard shell in the peripheral direction.

19. A sealing lip device as set forth in claim 15, wherein there is imparted to the sealing lip device a prestressing which is achieved by elastic deformation upon coupling to the hard shell.

20. A sealing lip device as set forth in claim 1, further comprising a frame portion extending substantially in one plane.

21. A sealing lip device as set forth in claim 20, wherein the frame portion is of a configuration which advances in a region of an articulation axis relative to a zone of high load-bearing capability.

22. A sealing lip device as set forth in claim 1, wherein a wall thickness of a thin zone of the sealing lip is in the range of between 0.65 and 1.85 mm.

23. A sealing lip device as set forth in claim 1, wherein the zone of high load-bearing capability is of a different color from the thinner-wall zone.

24. A mold for producing a sealing lip device as set forth in claim 1, wherein a mold core device which in conjunction with an outer mold defines a mold cavity with a fold portion for forming a portion of the sealing lip device having a varying degree of flexibility.

25. A mold as set forth in claim 24, wherein the outer mold is of a multi-part configuration.

26. A mold as set forth in claim 24, wherein the outside of a sealing lip, which in use is towards the mask wearer, is formed by an outer mold portion in conjunction with the mold core device, wherein the outer mold portion has a peripherally extending mold cavity channel which defines the outside of the sealing lip.

27. A mold as set for in claim 26, wherein the outer edge of the mold cavity channel extends in the region of the outer peripheral edge of the sealing lip.

28. A sealing lip device as set forth in claim 1, wherein the elastomeric material comprises silicone rubber.

29. A mask for delivering a flow of breathable gas to a patient, comprising:

a frame having a front side configured to be connected to a conduit for delivering the flow of breathable gas, and a rear side; and a cushion formed of elastomeric material and defining an internal space, the cushion having a front side configured to be attachable to and detachable from the rear side of the frame, the cushion having a rear side configured to engage the face of the patient in use, wherein the rear side of the cushion comprises a sealing lip having a peripheral edge defining a nose receiving opening configured to receive at least the patient's nose into the internal space, the sealing lip including a first zone configured to seal against the bridge of the patient's nose and two second zones configured to seal against the patient's face from the bridge of the patient's nose to areas adjacent the patient's nostrils and a third zone extending between the two second zones, the cushion further comprising a support wall extending from the front side to the sealing lip, the support wall being thicker than the sealing lip and comprising a first folding bellows structure extending at least along the first zone and the two second zones, the first folding bellows structure comprising a first fold indentation comprising two first fold flanks inclined relative to each other towards the internal space, the support wall comprising thickened wall portions in regions corresponding to the two second zones, the support wall further comprising a second folding bellows structure extending at least along the third zone, the second folding bellows structure comprising a second fold indentation comprising two second fold flanks inclined relative to each other towards the internal space, the cushion further comprising a groove provided on the front side configured to receive a peripheral portion of the frame when the cushion and frame are attached.

30. A mask as set forth in claim 29, wherein the frame comprises a plurality of projections configured to engage a periphery of the front side of the cushion when the frame and the cushion are attached.

31. A mask as set forth in claim 30, wherein the cushion further comprises a plurality of outlet openings configured to allow a flow of gas out of the internal space.

32. A mask as set forth in claim 31, wherein the plurality of outlet openings are tapered down in cross section from an interior surface of the cushion to an exterior surface.

33. A mask as set forth in claim 32, wherein ends of the first and second folding bellows structures are rounded.

34. A mask as set forth in claim 33, wherein the frame comprises a connector configured to connect a conduit configured to deliver the flow of breathable gas.

35. A mask as set forth in claim 34, wherein the frame comprises at least one fixture configured to receive a strap.

* * * * *